United States Patent [19]

Walling

[11] Patent Number: 4,945,410
[45] Date of Patent: * Jul. 31, 1990

[54] SATELLITE COMMUNICATIONS SYSTEM FOR MEDICAL RELATED IMAGES

[75] Inventor: Paul J. Walling, San Bernardino, Calif.

[73] Assignee: Professional Satellite Imaging, Inc., Colton, Calif.

[*] Notice: The portion of the term of this patent subsequent to Jan. 13, 2006 has been disclaimed.

[21] Appl. No.: 262,566

[22] Filed: Oct. 24, 1988

Related U.S. Application Data

[63] Continuation-in-part of Ser. No. 12,450, Feb. 9, 1987, Pat. No. 4,802,008.

[51] Int. Cl.$^5$ .......................... H04N 1/00; H04N 7/12
[52] U.S. Cl. ..................................... 358/141; 358/406; 358/134
[58] Field of Search ............... 358/141, 134, 257, 111, 358/133, 140, 256, 280; 128/903, 904; 455/12

[56] References Cited

U.S. PATENT DOCUMENTS

| | | | |
|---|---|---|---|
| 3,714,377 | 1/1973 | Moretti | 358/134 X |
| 4,492,978 | 1/1985 | Thomas | 358/134 |
| 4,494,141 | 1/1985 | Altekruse | 358/134 X |
| 4,694,338 | 9/1987 | Tsinberg | 358/141 |
| 4,802,008 | 1/1989 | Walling | 358/134 X |

OTHER PUBLICATIONS

"Single Frame Video: The Technology Behind UPI Newstime", Electro-Optical systems Design: vol. 10, #12; Dec. '78; pp. 24–29; Southworth.

Primary Examiner—James J. Groody
Assistant Examiner—Victor R. Kostak
Attorney, Agent, or Firm—Irell & Manella

[57] ABSTRACT

A satellite communications system for transmitting medical related images from one or more remote satellite locations to a central headquarters and then sending back diagnostic analysis from the central headquaters to the one or more remote satellite locations by having a high resolution camera and a video compressor for converting high resolution images into voltage analog signals, a modulator for converting the voltage analog signals into a narrow bandwidth and low frequency signal, a satellite system for transmitting and receiving images and analysis, a demodulator for converting the narrow bandwidth and low frequency signal back into a voltage analog signal, a video expander for converting the voltage analog signal into a digital signal, a buffer for buffering the digital signal, a high resolution monitor for converting the buffered digital signal into a high resolution digitized image.

12 Claims, 5 Drawing Sheets

FIG. 4.

SATELLITE COMMUNICATIONS SYSTEM FOR MEDICAL RELATED IMAGES

REFERENCE TO RELATED APPLICATION

This application is a continuation-in-part application of the patent application which is the subject matter of Ser. No. 07/012,450, filed on Feb. 9, 1987, the priority of which is claimed and the entire disclosure of which is incorporated herein by reference, now U.S. Pat. No. 4,802,008.

Field of the Invention

This invention relates to a satellite communications system for transmitting medical related images from one or more remote locations to a central headquarters and then sending back diagnostic analysis from the central headquarters to one or more of the remote locations and more particularly, to an apparatus and method for converting static, high resolution, video images into low frequency signals capable of being transmitted over a narrow bandwidth and for converting the low frequency signals back into static, high resolution, video images for analysis by a trained professional.

Background of the Invention

Systems are well known for sending medical related images, such as X-rays, ultrasound, computerized tomography (CT), nuclear magnetic resonance (NMR), EKG, etc., over phone lines and standard television communication systems. These existing medical communications system, however, suffer from a number of disadvantages, including high costs, immobility, inaccuracy, and slow transmission communication.

The cost of sending high resolution images over phone lines is expensive due to the high costs associated with operating a phone link system. Slow transmission rates over the phone lines (9600 baud rate maximum) further causes expenses to accumulate over time. Also, digitized images sent over phone lines must be encoded with extra parity bits to ensure against errors caused by noise (20 db signal to noise ratio) during transmission. Analysis of the extra bits causes further delay in transmission. Often, errors are not detected and the images are sent with the inaccuracies anyway. In these situations doctors are left with evaluating images that have inaccuracies. Thus, the analysis provided by the doctor is inadequate due to the inaccuracies of the image. Furthermore, phone link systems cannot easily provide communication to the remote locations. It is desirable to have each remote location capable of developing medical photographs and capable of sending the photographs from any location to a central headquarters, where these images can be diagnosed by a professional. However, phone link systems are constrained in that not all locations can provide the proper phone line hookups for sending the medical images to the central headquarters.

Fixed and/or mobile television communication systems are also used to send images from remote locations to central locations, however, these systems are very expensive to operate. Particularly, in situations where the remote locations are at large distances from the central headquarters, requiring expensive television type satellite communications equipment to complete the transmission. These systems are expensive because they transmit non-static type images highly used bandwidths at high frequencies. The higher the frequency, and the greater the bandwidth, the more it usually costs to transmit by satellite.

Due to the high costs and the problems associated with transmitting images over phone lines and/or standard television communications equipment, incorporation medical diagnostic equipment, with the capability of sending video images back to a central headquarters for analysis, has not been developed.

Summary of the Invention

The aforesaid difficulties are overcome by the present invention, which includes one or more remote locations having communication equipment for sending high resolution, medically related, static images over narrow bandwidth/low frequency signals to a central location for diagnosis.

More particularly, the system consists of means for converting a high resolution image into a voltage analog signal, means for converting the voltage analog signal into a narrow bandwidth/low frequency signal, means for transmitting the narrow bandwidth/low frequency signal to a satellite, means for receiving the narrow bandwidth/low frequency signal, means for converting the narrow bandwidth/low frequency signal back into a voltage analog signal, means for converting the voltage analog signal into a digital signal, means for buffering the digital signal, means for converting the buffered digital signal into a high resolution image, and means for transmitting diagnostic analysis, by a trained professional, in voice or readable form back to the sending unit.

By converting only static or single frame images, this invention overcomes the drawbacks of the prior art. Essentially, because the image does not move, (i.e., x-ray, etc.), the transmitting equipment can taken more time to break down the static image and it can send low frequency/narrow bandwidth signals at a slower rate, thereby reducing the cost of sending images traditionally associated with standard television communication systems. This invention uses the lowest possible frequencies and narrowest possible bandwidth to achieve the highest quality transmission of the images available, thereby keeping costs low. Additionally, the system can achieve the transmission more accurately at a 65 db signal to noise ratio and in less than 1/12 the time it takes a phone line system to operate.

The present invention allows remote satellite locations to efficiently and inexpensively send medical related images back to a central location for diagnosis. Thus, necessary medical care can be brought to patients at locations in the world, where the professional help may not be available.

Detailed Description

Figure 1A:
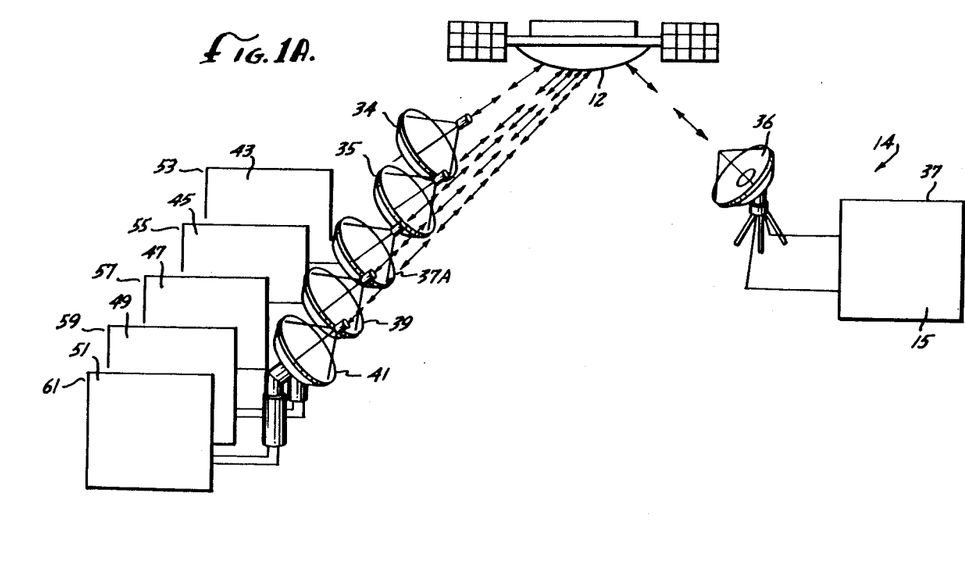
FIG. 1A shows multiple satellite locations sending stations equipped for sending and receiving low frequency/narrow bandwidth signals to and from a central headquarters in accordance with this invention.
Figure 1B:
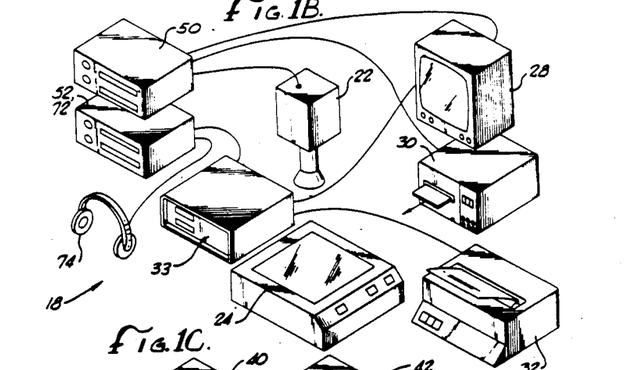
FIG. 1B is a parts diagram of the image conversion equipment located within one of the remote satellite locations.
Figure 1C:
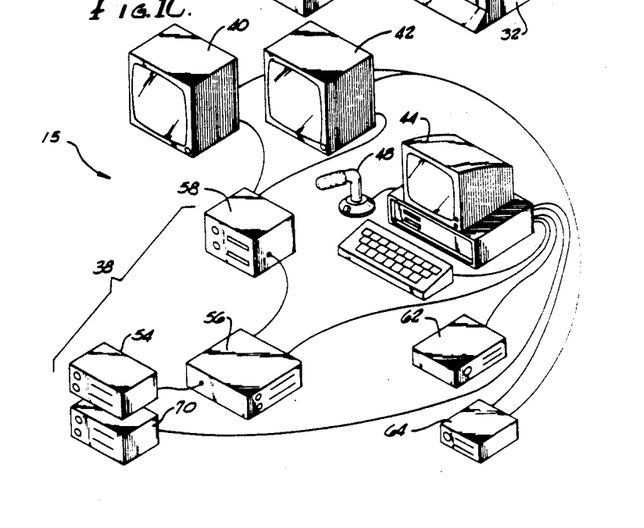
FIG. 1C is a parts diagram of the image conversion equipment located within the central headquarters.

Referring to FIGS. 1A, 1B and 1C, remote, fixed satellite locations 53, 55, 57, 59 and 61 are shown transmitting low frequency/narrow bandwidth signals to a satellite 12 which in turn transmits the low frequency narrow band signals to a central headquarters 14. Each satellite location 53, 55, 57, 59 and 61 contains equipment for generating medical related images, such as the X-ray equipment 16 as shown. The satellite location 53, 55, 57, 59 and 61 can also accommodate ultrasound equipment, magnetic resonance equipment, echo cardiogram equipment, etc. For discussion purposes only, however, we will focus primarily on transmitting photographic images produced by X-ray equipment 16. Although the remote satellite locations are shown together in FIG. 1A, they normally are spread several miles apart from one another across the United States and throughout the world.

Each remote satellite location 53, 55, 57, 59 and 61 contains image conversion and communications equipment 18. Referring to FIG. 1B, this equipment includes a receiving and transmitting satellite antenna control (not shown), a high resolution camera 22, a light table 24, monitor 28, thermal printer 30, impact printer 32, video compressor 50, modulator/demodulator 52 and 72, computer 33 and head phones 74. Each remote satellite location also includes a dark room for developing medical photographs (which is not shown). The top side of the remote satellite location includes a satellite antenna (34, 35, 37, 39 and 41) for communication with the central headquarters 14. Any number of remote satellite locations are capable of communicating with the central headquarters 14 or to other remote satellite locations from any given location throughout the world.

Central headquarters 14 consists of a receiving and transmitting satellite antenna 36 and headquarters 37. Referring to FIG. 1C, the equipment for analyzing the received radio signals from the remote satellite locations is shown. Receiving equipment 38, consisting of a demodulator 54, video expander 56 and buffer 58, is linked to monitors 40, 42 and to personal computer 44. The personal computer 44 is linked to mass storage 62, frame store 64, and modulator 70 which is linked to satellite antenna 36 in FIG. 1A.

Generally, referring to FIGS. 1A, 1B and 1C, the detailed operation of this satellite communication system is now explained. Each remote satellite location 53, 55, 57, 59 and 61 provides medical diagnostic equipment, i.e., X-ray equipment, etc., at any location and the information generated by the equipment can be analyzed at a central location. For example, the remote satellite locations 53, 55, 57, 59 and 61 contain medical equipment, such as X-ray equipment 16, which can take necessary x-ray photographs of any accident victim who comes to or is brought to the location. The remote satellite locations 53, 55, 57, 59 and 61 have the necessary facility for developing the X ray photographs and transmitting equipment for sending an image of the X-ray photograph to a central headquarter 14 for professional analysis.

More particularly, referring to FIG. 1B, an operator of the equipment takes a developed X-ray and places it on light table 24 for reviewing by a high resolution camera 22. High resolution camera 22 takes a video photograph of the X-ray and this image is converted into an analog voltage signal by video compressor 50. FM modulator 52 then converts the analog signal into a low frequency narrow bandwidth signal to be transmitted by satellite dish 34 (FIG. 1A). The signal is sent to satellite 12 where it is resent to the central headquarters satellite antenna 36. The remote satellite location and the central headquarters 14 can be at any distance from each other. For example, a remote location can be in the flat plains of the desert in Arizona which transmits images by satellite to a central headquarters located in Southern California. Doctors at the central headquarters can then return diagnostics, including medical instructions, etc. to the remote satellite location.

At the central headquarters 14 (FIG. 1A), the transmission signal is converted into an analog voltage signal by demodulator 54 and then converted into a digital image at video expander 56 (FIG. 1C). In the preferred embodiment, high resolution monitors 40, 42 are capable of displaying two different static (i.e. X-ray) images transmitted from the remote location. A radiologist, for example, can then review the images displayed on the high resolution monitors 40, 42 and provide his diagnosis of the X-rays directly to the remote location via satellite, in either voice or readable form. Microphone 48 converts the doctor's verbal diagnosis into an analog signal which is sent directly to FM modulator 70, where it is converted into a frequency signal to be sent over satellite antenna 34 (FIG. 1A) to the remote location. Additionally, computer 44 is capable of converting the doctor's verbal analysis directly into digital text, which can be separately FM modulated and sent to remote satellite locations.

Video expander 56 is also linked to personal computer 44 which is equipped with software algorithms for reformatting the digital data for long term storage on an optical disk 62. Personal computer 44 is linked to optical disk/mass storage 62 for retaining a permanent copy of the X-ray images. In addition, the diagnosis provided by the doctor is also storable on mass storage 62 in the form of digital text. The operator at the remote location will then see the diagnostic analysis on the printer 32 or hear the doctors voice via headphones 74 (FIG. 1B). Impact printer 32 will provide the operator with a hard copy of the diagnosis and thermal printer 30 will provide the operator with a detailed photographic copy of the X-ray. These hard copies can be used by an operator/paramedic for applying first aid to an accident victim or to a hospital nurse for record keeping purposes.

Figure 2:
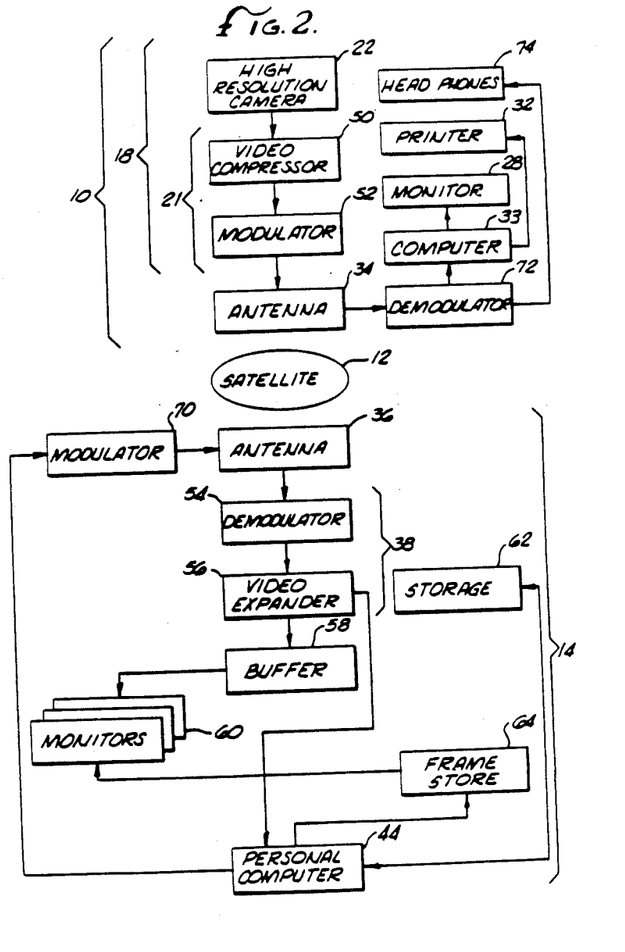
FIG. 2 is a schematic block diagram of the information flow from the high resolution cameras in the remote satellite location to the diagnostic monitors in the central headquarters for analysis.

Referring to FIG. 2, a block diagram representation of the preferred embodiment of the system is shown. As discussed above, the remote location consists of image conversation and communications equipment 18 and satellite antenna 34. The image conversation and communications equipment can be further broken down into high resolution camera 22 and transmission equipment 21. The transmission equipment includes a video compressor 50 and modulator 52. Starting with block 22, a high resolution photograph of, for example, an X-ray is taken. High resolution cameras are well known to those skilled in the art and in the preferred embodiment, the high resolution camera 22 is a 68-Series MTI™ camera designed and built by Dage-MTI Inc. In the preferred embodiment, the high resolution camera has 512 × 512 picture elements or pixels and for even higher resolution the camera has 1,024×1,024 pixels. Each picture element or pixel is essentially a small light detector for sensing the intensity of light at a given location. The more pixels there are on the charged coupled array (not shown) of the camera, the better the quality of the image recorded. The camera is also equipped with a focus and zoom control so that an operator can adjust the camera to obtain any desired view of the X-ray image. Additionally, it is envisioned that a doctor at the central location 14 (FIG. 1A) will be able to control the positioning, zoom and focus of the high resolution camera 22.

The high resolution camera is linked to transmission equipment 21 which converts the high resolution television signal into a narrow band with, low frequency signal so that a transmission can be made over the FM band. In the preferred embodiment, the transmission equipment 21 consists of a Video Compressor Series-262 provided by Colorado Video Inc. linked to a standard FM modulator 52. For a more detailed description of a video compressor, see Appendix I.

The video compressor essentially takes vertical row samples or an orthogonal scan of the high resolution video image provided by camera 22. As the camera scans each horizontal row of pixels once every 63 ½ microseconds, the video compressor samples one pixel per row. In this way, the video compressor scans the high resolution image in a series of vertical columns, scanning the image from left to right. It takes 1/60 of a second for a single vertical scan, from the top to the bottom of the high resolution image. An entire frame period or one scan from left to right of an image having 512×512 pixels takes about 16 seconds. A scan of an image having 1,024×1,024 pixels takes approximately four times as long. As the video compressor scans a high resolution image, an analog voltage signal (FIG. 3) is produced and simultaneously sent to FM modulator 52.

Figure 3:
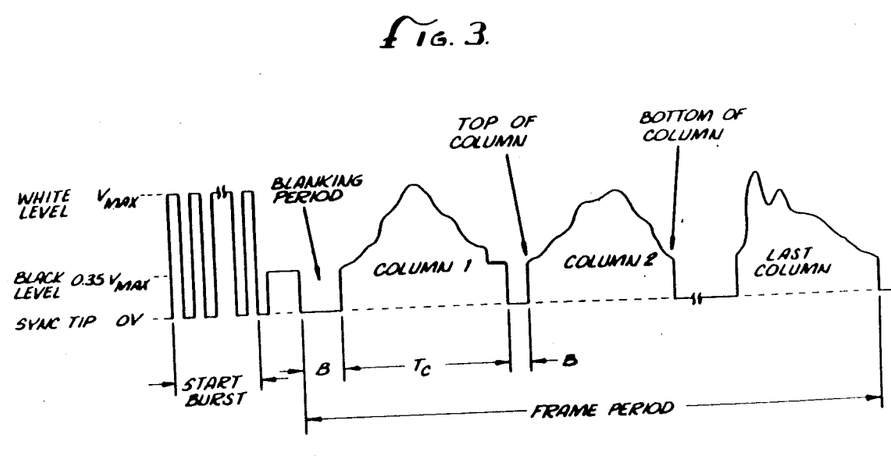
FIG. 3 is a plot of the voltage analog signal produced by the video compressor prior to FM modulation.

Referring to FIG. 3, the left hand column of the signal graph shows a gray scale (white to black levels) and a voltage scale for each level of light detected by a pixel. When the pixel detects a very dark or black image, the video compressor sends an analog voltage signal of 35 volts to the FM modulator. When the gray scale detected by the pixel is very light or almost at a white level, the video compressor sends an analog signal near its peak voltage. In other words, for each pixel, a gray value is represented by a particular voltage and the pixels are capable of detecting 256 levels of gray, from very light to very dark.

Now referring more particularly to the voltage signal represented in FIG. 3, at the left hand side, a start burst or square wave is depicted. This start burst essentially tells the receiver 38 (FIG. 2) to get ready for a transmission. A delay of a few seconds is then allowed to enable the receiving equipment to get ready for a transmission. An impulse of 35 volts alerts the receiving equipment that an analog voltage signal representing the gray scale of the pixel, in column I (left most column) is being sent. Scanning a column of 512 pixels typically takes 1/60th of a second and a very short blanking period at 0 volts is followed. The beginning the analog signal (FIG. 3) represents the top of the column of pixels and the end of the analog signal represents the bottom of the column of pixels. Each column is depicted by a separate analog signal, separated by a short blanking period of 0 volts.

As stated, when the analog signal is being generated by the video compressor it is also simultaneously sent to the FM modulator 52. The FM modulator essentially converts this voltage analog signal into a frequency signal which is acceptable for standard radio transmission equipment. In the preferred embodiment, the zero voltage range of the voltage analog signal is represented by an 11 KHz bandwidth signal and the maximum voltage is represented by a 15 KHz signal.

Essentially, the remote location 53 acts as a standard FM radio station, converting the 11-15 KHz bandwidth signal into an FM transmission. The frequency signal representative of the voltage analog signal is sent via a satellite antenna 34 at approximately an occupied bandwidth of 180-200 KHz bandwidth. At this bandwidth, the noise to signal ratio of the system is 65 db. For a lower noise to signal ratio a greater deviation from the 11-15 KHz signal is made (e.g. 220-246 occupied bandwidth signal). Satellite 12 essentially acts as a repeater translating the transmitted signal into a different frequency and then sending it to satellite antenna 36 at central headquarters 14. The satellite antenna 36 is equipped with an FM filter to ensure that the receiving equipment only receives the transmitted signals from the satellite. For a more detailed description of satellite dish antenna 34, 36 and satellite 12, refer to Appendix II. The signal is then sent to the receiving equipment 38 where demodulator 54 converts the frequency signal back to an analog voltage signal.

Video expander 56 converts the voltage analog signal into a digital signal. This digital signal is temporarily stored in a buffer 58 until enough data is accumulated to be properly read out to the high resolution monitors 60. The high resolution monitors require that each column of pixels be built within 1/60 of a second. The receiving equipment, however, does not process the pixel data fast enough to create a pixel column in 1/60 of a second. Thus, the buffer 58 provides the necessary time delay for the digital data to accumulate before the columns of pixels can be developed on the high resolution monitors 60. High resolution monitors are well known to those skilled in the art and in the preferred embodiment, the high resolution monitors are HR series 2000 provided by Dage-MTI Inc. These monitors were specifically designed for viewing X rays, and other medically related images.

For maintaining a permanent copy of the transmitted image, video expander 56 is linked to a personal computer equipped with software which reformats the digital data for storage on a standard mass storage electronic device. In the preferred embodiment, this storage device is an optical disc, however, any mass storage device for large amounts of digital data is suitable. The optical disc stores the X-ray images in digital form for any desired length of time. When the X-ray information is needed at a later date, the digital data can be easily retrieved from the optical disc by a command from computer 44. Because the digital data is stored on optical disc in a computer oriented format, it is not suitable for sending directly to the high resolution monitors 60. For this reason, a frame store 64 is provided for converting the stored digital computer data into a format that the high resolution monitors can interpret.

Essentially, frame store 64 is an intelligent buffer for temporarily storing the digital data in its own memory and converting it into a format to be shown on the high resolution monitors 60. For a more detailed discussion of the frame store 64, please refer to Appendix III. In the preferred embodiment, the frame store is a Serial No. 491 Video Frame Store provided by Colorado Video Inc.

When the digital data is displayed on monitor 60, a doctor analyzes the displayed image and provides his diagnosis via a voice activated computer 44. An analog voice signal of the doctor's diagnosis is sent to modulator 70 for transmission or a digital text signal is sent to modulator 70 for transmission back to the remote location 53.

Additionally, the digital text signal is also sent to the mass storage device 62 for storage and/or future reference. For transmission of the diagnosis to remote location 53, modulator 70 converts the voice or digital signals into a narrow bandwidth/low frequency signal. Satellite dish antenna 36 then transmits the frequency signal to the satellite 12 which in turn repeats a different frequency signal to the satellite antenna 34 of remote location 53. The narrow bandwidth/low frequency signal representative of the voice signal or the digital text signal is then converted back to an analog or digital signal by demodulator 72 on remote location 53. The digital text signal is processed and formated by computer 33 and then it is displayed on a standard monitor 28 or printer 32, the textual analysis is provided to printer 32, so that the operator has a record of the diagnosis. If voice signals are sent, then the analog voice signal is sent from demodulator 72 directly to head phones 74. The instructions and analysis provided by the doctor will then be used by the operator/nurse to administer treatment if necessary.

Figure 4:
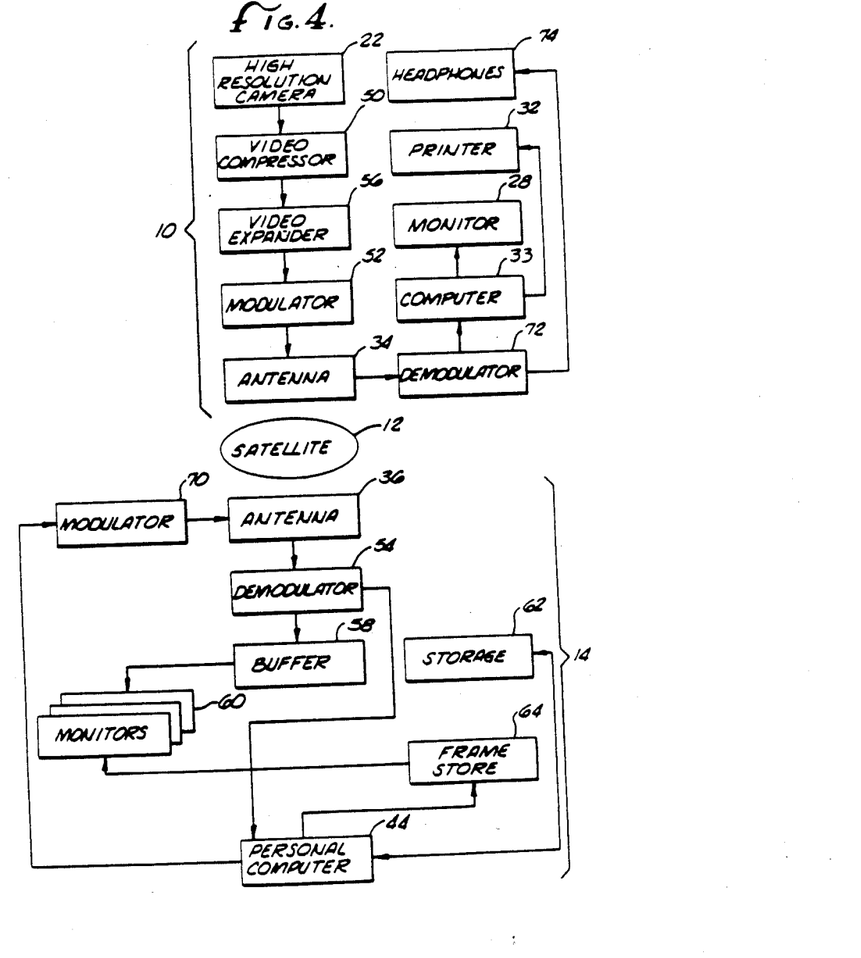
FIG. 4 is a schematic block diagram of the information flow in a second embodiment of the invention.

Up until now, a satellite communications system for sending narrow bandwidth/low frequency signals representing voltage analog signals of video images has been described. Referring to FIG. 4, another embodiment is depicted for transmitting a frequency signal representative of a digital signal instead of a voltage signal. The only difference in the embodiments depicted in FIGS. 2 and 4, is that the video expander has been moved from the central headquarters 14 into the remote satellite locations. Now when the video compressor 50 generates a voltage analog signal a video expander 56 will convert the analog signal into a digital signal. As mentioned previously, the voltage analog signal produced by the video compressor represents pixel gray scale values for the vertical columns of pixels in the high resolution camera. The video expander converts the voltage signal into a binary number from 0 to 256. Each binary number represents a digital signal to be converted by the FM modulator 52 into a narrow band/low frequency signal. Essentially, the video expander acts as an analog/digital converter, changing the voltage signal of the video compressor into a digital signal for FM modulation. Satellite antenna 34, on remote satellite locations, sends the narrow band/low frequency signal to satellite 12. Satellite antenna 36 at the central headquarters 14 receives the signal reflected by the satellite 12. The frequency signal is then converted into a digital signal by the demodulator 54. Unlike the other previously described embodiments, a video expander need not be provided because the signal is already represented in its digital form. However, a buffer is still required to delay the data before it is sent to monitors 60. All other parts of this embodiment are identical to the embodiment shown in FIG. 2.

APPENDIX I—VIDEO COMPRESSOR

Purpose of Equipment

The Video Compressor is intended to function as the transmitter in a narrow-band (sometimes called "slow-scan") video communications system. It accepts a standard, composite TV signal and reduces the signal bandwidth to the audio range for transmission over narrow-band communication channels. The video compressor requires a channel bandwidth of 11–15 KHz and transmits a picture in 9 to 30 seconds depending on the resolution required. The video compressor operates over voice grade FM modulated band frequency channels and requires 8 seconds for 256×256 resolution, 16 seconds for 512×512 resolution.

A Video Expander is usually used at the receiver end of the channel to store and display the transmitted image.

Description of Equipment

The Video Compressor is a sampling scan converter which accepts standard, composite TV signals and reduces the video bandwidth to the audio range. The sampling format is one sample per TV scan line starting in the upper left corner of the raster and forming a vertical column. The output slow-scan signal with a line rate equal to the field of the input TV signal (60 lines/second for U.S. standards), and scans vertically from top to bottom. The frame rate depends on the TV line rate and on the desired resolution and scans from left to right.

The bandwidth of the output signal is approximately 11–15 KHz (15,750 samples/second for U.S. 525-line standards). The output signal is DC coupled and follows the TV convention of whites being positive going. Vertical resolution is equal to that of the "real-time" input TV signal, while the horizontal resolution is determined by the slow-scan frame time.

A special feature of the Video Compressor is a "real time" monitor output signal that displays the sampling column and the resultant slow-scan video wave form superimposed on the input video. Before transmitting a picture, the operator can move this column across the picture to determine and adjust the quality of the slow scan output signal. During transmission, the sampling column moves slowly from left to right indicating the portion of the picture remaining to be transmitted.

Specifications

| | |
|---|---|
| Size: | 5½" × 17" × 13" |
| Weight: | 11 lbs. |
| Mounting: | Stand alone (rack mount optional) |
| Power: | 117/230 VAC, 50/60 Hz, 20 VA |
| Input: | Composite video; 1 volt p-p, 75 ohms (525-line or 625-line, 2:1 interlace) |
| Outputs: | Slow-scan video; adjustable 0 to 6 volts max., 600 ohms, white positive |
| | Video; Composite, 1 V p-p, 75 ohms |
| Controls: | Video Level |
| | Black Level |
| | Output Level |
| | Analyze (position) |
| | Single/Continuous (Optional) |
| | Start |
| Connectors: | Video, BNC |
| | Slow-scan output; 5 pin, Amphenol 126 series |
| Performance: | Band width; 4 MHz monial, to match receiver resolution capability and to minimize noise. |
| | Frame Period; 4.27 or 8.53 seconds (525-line/60 HZ) 5.12 or 10.24 seconds (625-line/50 Hz) |

Output Signal Characteristics
The output signal characteristics are:

-continued

| Type: | Baseband, narrow-band video formatted. |
| --- | --- |
| Level: | Can be adjusted using front panel OUTPUT LEVEL control up to 6 volts p-p when connected to a 600 ohm transmission line. Connect oscilloscope to TP2 to monitor output signal level. |
| Spectrum: | DC to 15 KHz. Maximum energy at 60 Hz (50 Hz for 625-line TV source and multiples thereof. |
| Typical Systems Responses | |
| Frequency Response: | 11 to 15 KHz |
| Signal-to-Noise Ratio: | 60 db or better |

Operation

Single Frame Operation In most instances, such as person-to-person communications of visual material, it is desirable to send pictures one frame at a time. Typically, a vidicon camera will be used as a video input source to the Video Compressor and the "real-time" signal will be viewed On a conventional TV monitor. The operator may thus compose to his satisfaction the image to be transmitted, ensuring that it is properly focused and clearly shows significant detail. Following a convention widely used in broadcast studios, it is preferable not to attempt to show too much detail, and closeups of subjects are to be preferred.

If a camera with automatic level control is used, adjustment of the BLACK LEVEL and VIDEO LEVEL controls should not be required after the initial adjustment. If more than one video camera is used, the output levels of all the cameras should be set to the same level if possible.

Once a satisfactory "real-time" picture is obtained, the START button is momentarily depressed to initiate transmission of that frame. The position of the sample line indicates the degree of transmission, and neither the camera nor the subject should be moved while the transmission is in progress When the transmission is complete, the sample line returns to mid-screen (or other position set by the ANALYZE control). Although another picture may be transmitted immediately, it is important to remember that the viewer at the receiving end may wish to spend some time observing the image that was just completed.

Continuous Scan Operation

When unattended operation is desired, such as for surveillance purposes, the SINGLE/CONT switch should be placed in the CONT position, and the Video Compressor will continuously transmit the input video signal. Again a reasonably constant input signal is desired, and cameras with automatic level control are recommended. The Video Compressor will tolerate a limited amount of motion in the scene being viewed, although geometric distortion in the reproduced image will occur in the following ways: objects moving right to left will be compressed, objects moving left to right will be expanded unless moving rapidly, in which case their direction of travel will seemingly be reversed. Objects moving vertically will be distorted diagonally, with the left hand side of subjects moving upward being lower than the right hand side, and the reverse holding for subjects moving downward.

Tape Recording

By using a tape recorder, it is possible to store a large number of pictures at the transmit end for subsequent transmission, or to store images at the receive end for subsequent viewing on a monitor. When making recordings, care should be taken in setting recording levels properly.

| Control | Function |
| --- | --- |
| CONTROLS | |
| Operating Controls (Front Panel) | |
| VIDEO LEVEL | Controls the amplitude of the input video to the internal sampling circuitry. Normally set so that the signal from the whitest portions of the picture causes the sampled waveform to touch the right calibration marker of the waveform display. |
| BLACK LEVEL | Controls the point on the input signal that is converted to a black output signal. Normally set so that the blackest portions of the picture cause the waveform to touch the left calibration marker of the waveform display. Set this control first, then the VIDEO LEVEL control. |
| ANALYZE | Controls the position of the sample line when the unit is not scanning. Use this control to analyze the brightness content of a picture in order to set the BLACK LEVEL and VIDEO LEVEL controls. |
| OUTPUT LEVEL | Controls the amplitude of the signal at the output terminals. Adjust for proper level by monitoring TP2 with an oscilloscope. Adjustment should be made after the transmission line or other device has been connected to the output terminals. |
| SINGLE/CONT | SINGLE position requires the operator to manually initiate the transmission of each frame. CONT position causes the 262 to automatically repeat the scan with an interval of several seconds between scans. |
| START | A pushbutton which is momentarily depressed to initiate the transmission of a single frame when the SINGLE/CONT switch is in the SINGLE position. |
| INTERNAL CONTROLS | |
| Scan Time | Controls the scan period for transmission of one frame. |
| Scan Centering | Controls the starting position of the sample line. Set to start at left-hand edge of raster. |
| Gain | Controls the gain of the waveform pulse position modulator. Set so that black-to-white just fills the space between the calibration lines. |
| Position | Controls the position of the waveform trace with respect to the calibration lines. |
| Waveform | Controls the brightness of the Brightness waveform trace. |
| Balance | Two controls used to equalize the gain of the two CCD converter sections of U10. Set for matching output levels as indicated by a single (not split) trace at the output of AR1C. |
| Line Sync Amp | Controls the amplitude of line sync added to the sampled video. Set for two parts ideo to one part line sync. |
| Deviation | Controls the gain of the FM modulator. Adjust for 1.6 to 2.4 KHz output signal when input signal goes from full black to full white. |
| Frequency | Controls the center frequency of the FM modulator. This control and the deviation control interact, so proper adjustment of the frequency deviation will require going back and forth between them several times. |
| Video Level | Adjusts the video level of the 8 KHz |

| Control | Function |
|---|---|
| | signal to the converter board. |

APPENDIX II—SATELLITE EQUIPMENT

(II-A) Dish Antenna Development

General Operation

The dish is stowed and deployed by a hydraulic ram that is powered by a 12 VDC motor driven pump drawing approximately 200 Amperes. Limit switches are provided to stop deployment when the operating position is reached. Dish storage and deployment are accomplished automatically by the AP-1 unit.

The azimuth adjustment is effected by a 120 VAC motorized gear drive. A limit switch is located at each end of the horizontal dish travel. Two limit switches are used to center the dish prior to stowage. Dish elevation is accomplished by a 120 VAC motor driven screw jack. Limit switches permit adjustment between 0° and 90° elevation. A 120 VAC motorized gear drive provides polarizing adjustment of the freedom.

| | | |
|---|---|---|
| Deployment | (1) | To raise the dish antenna from its storage position to its operational position, first select the power system to be used. When connected to shore or auxiliary generator power, first verify that the "utility light" breaker on the Power Distribution Panel is on. Next move the "Pan-Tilt Power" switch on the Power Distribution Panel to the AC position. If the truck is not connected to the shore power and the generator is not being used, move the "Pan-Tilt Power" switch to the Inverter position. |
| | (2) | To enable the system, lift the red enable switch guard on the Hubcom AP-1 "Deploy" section and move the toggle switch to the right. |
| | (3) | Depress the "UP" button located beneath the enable switch until the dish antenna is raised to its full operational position and stops automatically. |
| Aiming | (1) | To adjust the dish azimuth, press the "CCW/CW" switch in the azimuth section of the AP-1, for counter-clockwise rotation of the dish assembly. A digital readout will monitor the dish azimuth heading in degrees as it is moved. The "F/S" switch in the azimuth section selects a fast or slow azimuth adjustment speed. |
| | (2) | To adjust the dish elevation, depress the "UP/ON" switch in the elevation section of the AP-1 until the desired elevation is displayed in degrees in the digital readout. The "F/S" switch in the elevation section selects fast or slow elevation adjustment speed. |
| | (3) | It is necessary to know the polarization of the desired transponder prior to transmission. The "V" or "H" buttons on the Hubcom MS-2 will then route the wave guides to provided the corresponding vertical or horizontal feed port for the received signal. The transmitted signal will be automatically routed to the orthogonal feed port. |
| | (4) | Once the proper receive polarization is selected, the feedhorn position can be fine tuned over a +45° angle by depressing the "CCW/CW" switch in the polarity section of the AP-1 until the best signal is obtained. Use the "F/S" switch in the polarity section to select fast or slow polarization adjustment speed. |

To return the dish antenna to the storage position, simply depress the "stow" button on the "AP-1" unit. The dish antenna will center and lower itself to the storage position automatically.

Dish antenna positioning is controlled from the operator area and is greatly simplified by digital readouts of elevation and azimuth on the dish aiming control panel. Once the dish is roughly positioned, the transponder frequency selected and correct polarization of the feedhorn chosen watch the spectrum analyzer while slowly panning the dish in a systematic pattern until a sight display of an active transponder is seen. All satellites have characteristic spectral energy distribution. Check for narrow band communications channels, half transponder operation, scrambled signals and narrow band beacons.

To scan satellites in the Eastern hemisphere, at a longitude greater than that of your location, lower on the dish until the spectrum analyzer display flattens out, pan left to the next satellite or raise the dish to flatten the display and pan right. If the longitudes are close to equal lower the dish very little and pan left or right of the satellite longitude is less than that of your location, lower the dish and pan right or raise the dish and pan left.

To scan satelitte on the Western hemisphere, greater than that of you own location, lower the dish until the spectrum analyzer display flattens out, pan right to the next satellite or raise the dish to flatten the display and pan left. If longitude close to equal, lower the dish very little and pan left or right. If the satelitte longitude is less than that of your location, lower the dish and pan left or raise the dish and pan right.

Once the correct satellite is found, fine tune the dish position by optimizing the amplitude of the spectral display. The video waveform monitor can be used to clean up the top of the sync pulse on unscrambled channels as a means of fine tuning.

(II-B) RF Terminal

The terminal transmits at 14.0–14.5 GHz and receives at 11.7–12.2 GHz. It consists of a microwave tranceiver, power supply unit, and ac and dc cables.

The preferred RF terminal is an ASAP 12161 Terminal provided by Avantek designed to interface with any modern dish having a data capability of 9.6 kbps to 1.544 <bps and any size antenna. It is used in a wide range of data distribution and collection applications, including financial data transfer, oil well and pipeline monitoring, point-of sales systems, electronic funds transfer, electronic mail, voice store-and-forward communications, and video conferencing.

The function of the ASAT 1214 RF Terminal is the upconversion of the modulators's IF output to an RF signal for transmission via an antenna, and the downconversion of the received RF signal for use by the demodulator. Major components are an upconverter chain, a low-noise downconverter, and a frequency synthesizer. The power amplifier in the upconverter chain is made of Aventek's Gallium Arsenide Field Effect Transistor (GaAsFET) devices and Internal Matching network (IMFET) devices that provide highly stable power gain and minimal intermodulation distortion. The downconverter is built around low-noise amplifier devices, providing a system noise temperature of better than 250.K. The synthesizers rely on an ovenized 10 MIIZ crystal oscillator which provides fully synthesized carrier frequency selection in 1 MHz steps over a 500 MHz bandwidth.

RF Transceiver

The RF transceiver, upconverts a 70 MHz IF signal from a modulator to a 14 GHz transmit signal. The upconversion process used two upconverters, a bandpass filter, and a power amplifier, and is controlled by an automatic level control (ALC) circuit. On the receive side, the transceiver downconverts a 12 GHz received signal to a 70 MHz IF signal for output to a demodulator. Key downconversion modules are a 12 GHz bandpass filter and a low-noise converter. Both conversion functions rely on LO signals processed by a fixed synthesizer. The system parameters are monitored by an internal summary alarm board.

The IF transmit signal enters the transceiver at a frequency of 70 MHz ±20 MHz. In the first upconverter, this IF signal mixes with a 1150 MHz LO signal to produce a 1220 MHz (±20 MHz) IF signal. After passing through a 1220 MHz bandpass filter, the signal is mixed in the second upconverter with a 12.78–13.78 GHz agile LO signal. When summed with the IF signal, the LO signal will produce a transmit signal with the desired RF frequency in the 14.0 14.5 GHzband.

The RF transmit signal is amplified by the power amplifier as a final step before transmission. Active bias regulators in the power amplifier ensure that each stage of amplification is performed at very nearly the optimum point regardless of temperature environment. A 2 W power amplifier raises the RF signal to the output power of 23 dBm to 33 dBm, depending on the setting selected during alignment. The selected output level is held constant by the automatic level control loop, consisting of a control circuit in the first upconverter and a level detector in the power amplifier.

Downconversion

The incoming 11.7–12.2 GHz receive signal passes through a 12 GHz low-insertion-loss bandpass filter. The filtered signal enters the low-noise converter which contains a low-noise amplifier, another filter, and two downconverters. The first downconverter mixes the receive signal with an agile LO signal at a frequency of between 12.78 and 13.28 GHz such that the produced IF signal will be 1080 ±20 MHz. The new IF receive signal is filtered and mixed in the second downconverter with a 1150 MHz LO signal for conversion to a 70 ±20 MHz IF signal. A low-noise amplifier performs final amplification of the IF signal.

LO synthesizers

The LO signals that are mixed with the transmit and receive signals are supplied by fixed and agile frequency sythesizers. The synthesizers use a 10 MHz ovenized crystal oscillator, designed for very low phase noise and high stability, as a reference. A X4 multiplier is used by the agile synthesizer. The signal produced by the agile synthesizer is made accessible to the customer through DIP switches that can be used to set the frequencies, and through a screw on the crystal oscillator for fine tuning. The synthesizer provides selection of transmit and receive frequencies, in 1 MHz steps, over the 500 MHz band.

Summary Alarm Board

All of the transceiver's functions are monitored by alarm circuitry which activates light-emitting diodes (LEDS) on the summary alarm board. The LED alarms allow detection of power failure, loss of lock, extreme temperature, and failure of any one of the functional components in the transceiver.

| Upconverter | |
|---|---|
| INPUT | |
| Frequency | 70 ± 20 MHz |
| Level | −30 dBm ± 4 (75 ohm) |
| Bandwidth | 40 MHz (IF) |
| OUTPUT | |
| Frequency | 14.0–14.5 GHz |
| Power (2 W Power Amp) | +33 dBm @ 1 dB comp. |
| Spurious | −60 dBc at rated power |
| AM/PM Conversion | 3./dB at rated power |
| Intercept Point | +41 dBm |
| VSWR | 1.25 (50 ohm) |
| Downconverter | |
| INPUT | |
| Frequency | 11.7–12.2 GHz |
| Level | −80 to −127 dBm |
| System Noise Figure | 2.7 dB (250.K) |
| VSWR | 1.2 (50 ohm) |
| OUTPUT | |
| Frequency | 70 MHz ± 20 MHz |
| IF Bandwidth | 40 MHz |
| Intercept Point | +22 dBm |
| VSWR | 1.5 (75 ohm) |
| Spurious Out | −85 dBm |
| GAIN | |
| Gain | 85 dB ± 3 dB @ 25° C. with 30 dB manual attenuation |
| Gain Flatness | ±.5 dB/40 MHz |
| Gain Stability | ±2.5 dB over temperature range |

(II-C) Satellite Network

In the preferred embodiment, the satellite system is a owned and operated by GTE Satellite Communications, and it is composed of three orbiting satellites. GStar A1 was successfully launched by an Ariane rocket on May 7, 1985. GStar A2 is scheduled to be launched in December 1985 or January 1986. These satellites are the first U.S. Ku-band communications spacecraft to offer 50-state coverage at 12 GHz, as well as regional beam coverage to the eastern or western halves of the continental United States. The GStar A2 and A3 satellites will also have the ability to transmit by way of two, high-powered spot beams.

Each GStar satellite carries 16 transponders with usable bandwidths of 54 MHz. Fourteen 20-watt transponders can be switched between east or west regional beams or CONUS coverage. The remaining two 27- watt transponders are connected to a combined footprint that covers CONUS, Alaska, and Hawaii. Because of their wide bandwidths, GStar transponders are capable of transmitting two simultaneous TV programs on multiple data and voice circuits.

Fourteen of GStar's 16 operational transponders use 20 watt TWTAs that can be tailored by ground command to provide east or west regional coverage or 48-state (CONUS) coverage. The remaining two transponders provide 50-state coverage using combined CONUS/Alaska/Hawaii beams powered by 27 watt TWTAs. The antenna subsystem comprises two offset parabolic reflectors. Polarization purity is achieved through the use of grids embedded in each reflector that are transparent to the opposite sense of polarity.

Efficient use of the communications capacity of these satellites will be obtained through digital transmission techniques. Customer-generated inputs will be digitalized prior to transmission through the system; a time division multiple access (TDMA) scheme will take the digitalized signals and integrate them into what is known as a "burst mode" delivery system. Periodic frame reconfiguration allocates satellite capacity in proportion to the traffic requirements of each earth satellite.

Another embodiment of the satellite network is a Hughes Galaxy which operates a Ku-band satellite system starting in 1987. The system consists of two in-orbit satellites providing coverage of the 48 contigous states. Hughes Galaxy receives orbital assignments of 71 and 180 degrees west longitude. Galaxy K-band satellites will use the Hughes Aircraft HS 393 wide-body design derived from the Intelsat VI spacecraft bus. Individual satellites within the system carry 16 active transponders with usable bandwidths of 52 MHz. Each transponder is connected by ground command to one of two shaped full-CONUS beams, or to an east or west half-CONUS beam.

APPENDIX III—VIDEO EXPANDER

The Video Expander is designed to operate over FM band frequencies. If a dedicated channel is used, the channel should have the following characteristics:

| | |
|---|---|
| Frequency Response: | 11 to 15 Khz |
| Signal-to-Noise Ratio: | 30 db or better |

In the receiving mode, the Video Expander accepts properly formatted slow-scan TV input signals and reconstructs a conventional TV still picture using the same memory which provided frame freeze for transmission. Image retention is indefinite unless deliberately erased or power to the Video Expander is lost. A remote control box is provided for easy desk top operation. The unit can be generally locked to other video sources to provide switching, mixing, and special effects capabilities.

| Specifications | |
|---|---|
| Size: | Main Chassis 3½" × 17" × 13" |
| | Single Memory Table Top 5¼" × 19" Multiple Memory Rack Mount |
| | Remote Control 8" × 6" × 2½" |
| Weight: | 15 lbs. Single Memory |
| Construction: | Solid state, card file |
| Power: | 117 VAC, 60 Hertz, single phase, 75 VA |

| -continued | |
|---|---|
| Specifications | |
| Inputs: | Receive: |
| | Slow-scan video: FM modulated carrier, 100 millivolts minimum level, 600 ohms, balanced |
| | Transmit: |
| | Composite video: 1 volt, 75 ohms, 2:1 interlace (3 inputs) |
| Outputs: | Receive & Transmit: |
| | Composite video: 1 volt p-p, 75 ohms, 2;1 interlace |
| | Transmit: |
| | FM modulated carrier, 1500 to 2400 Hertz, 0 to 2 volts p-p internally adjustable, 600 ohms, balanced |
| Controls: | Remote Control: |
| | Fast/Slow Rate |
| | Video Source: 1-2-3 |
| | Transmit Start |
| | Freeze |
| | Reset |
| | Receive Start |
| | Multiple Memory Unit Only: |
| | Write: 1/2/or more |
| | Display: 1/2/or more |
| | Main Chassis: |
| | AC Power |
| | Single/Continuous Transmission |
| | Video Level |
| | Black level |
| | Indicators: |
| | Scan |
| | Black Level |
| | White Level |
| Connectors: | BNC-Video |
| | 5 Pin Amphenol - Transmission Line |
| | 14 Pin Blue Ribbon - Remote Control |
| Performance: | Resolution: |
| | Slow speed: 256 × 256 picture elements; TV test chart resolution is 270 lines |
| | Fast speed: 256 × 256 picture elements; repeats same data in both fields; TV test chart resolution is 135 lines |
| | Option: |
| | 512 × 512 picture elements, dot interlace Frame Time: |
| | 74 seconds for full resolution |
| | 34 seconds for medium resolution |
| | 148 seconds for high resolution option |
| | Grayscale: |
| | 6 bits (64 gray levels) |
| | Option: 8 bits |
| Options: | Receive Only |
| | Transmit Only |
| | Frame Freeze Only |
| | Multiple Memories |

Operation

(General)

The Video Expander has two transmission rates. When the FAST/SLOW switch is in the FAST position, a single field picture with. 256×256 elements is transmitted approximately 34 seconds. When the switch is in the SLOW position, a full frame picture with 256×512 elements, dot interlaced, is transmitted in approximately 74 seconds. Both Video Transceivers must be set to the same speed for proper operation.

The SINGLE/CONT at the transmitter only must be in a position for the desired mode of operation as explained below.

Single Frame—Transmit

In many instances, such as person-to-person communication frame at a time on command. For this mode of operation, the SINGLE/CONT switch should be set to SINGLE.

Typically, one or more TV cameras will be used as the video input sources to the video expander and the "frozen" signal will be viewed on one or more conventional TV monitors. The operator may thus compose to his satisfaction the image to be transmitted, ensuring that it is properly focused and clearly shows significant detail.

When the transmission is complete, the cursor stops at the right hand edge of the raster and the scan light goes off. Although another picture may be transmitted immediately, it is important to remember that the viewer at the receiving end may wish to spend some time observing the image that was just completed.

Single Frame—Receive

For single frame reception, the video expander at the receive end should have its FAST/SLOW switch in the same position as the transmitting video expander.

When a start burst signal is received from the transmitter, the scan lights go on. As each column is received from the transmitter, it is stored in the 290 memory and displayed as a new column on the television monitor. Thus a new picture will build up, a column on the television monitor. Thus a new picture will build up, a column at a time, as the cursor moves from left to right across the raster.

Continuous Scan Operation

When unattended operation is desired, such as for surveillance purposes, the SINGLE/CONT switch on the transmitting video expander should be placed in the CONT position. The unit will then transmit a continuous sequence of pictures, freezing a new frame (field) each time.

The receiving video expander is set up in the same manner as for single frame operation, as described in the preceding section.

Memory

By using a memory device, it is possible to store a large number of pictures at the transmit end for subsequent transmission, or to store images at the receive end for subsequent viewing on a monitor.

| | | Controls Operating Controls - Chassis | | |
|---|---|---|---|---|
| | | | Use | |
| | Control | Function | Transmit | Receive |
| | Power | ON/OFF switch with internal pilot light to indicate when unit is on. | X | X |
| | Black Level | Controls the DC level of the video signal going to the internal A/D converter. Usually set so that detail in the black portions of the input signal are not lost. | X | |
| | Video Level | Controls the amplitude of the video signal going to the internal A/D converter. Usually set so that white details of the input signal are not compressed. | X | |
| | Single/Cont. | SINGLE position requires the operator to manually initiate the transmission of each frame. CONT position causes the 290 to automatically refreeze and scan with an interval of one second between scans. | X | |
| | Fast/Slow | When set in the FAST position, the 290 transmits or receives a singlefield picture in 34 seconds. When set in the SLOW position, a fullframe picture is transmitted in 74 seconds. | X | X |
| | Source | Selects the video input signal sent to the freeze circuitry. Position 1 selects VIDEO IN 1, etc. | X | |
| | Freeze | Momentary pushbutton that initiates the A/D conversion and storage | | |

-continued

| Control | Location | Function | | |
|---|---|---|---|---|
| | | of one frame of video from the selected source. When this pushbutton is held down, a continuous real-time display of the selected input signal will be displayed on a monitor connected to the VIDEO OUT connector. | | |
| | Transmit Start | Momentary pushbutton that starts the transmission (scan) process when the SINGLE/CONT switch is in the SINGLE position. | X | |
| | Reset | Momentary pushbutton that terminates the transmission or reception. | X | X |
| | Receive Start | Momentary pushbuttom that starts the receive process if for some reason the start burst was missed. | X | |

| | | | Use | |
|---|---|---|---|---|
| Control | Location | Function | Transmit | Receive |
| Line/ Gen/ XTAL | Sync & Timing BD | Selects the synchronizing source for the internal sync generator. In the LINE position, the 290 timing is synchronized to the power line frequency. In the GEN position, the timing is synchronized (genlocked) to the sync information of the selected video input. In the XTAL position, the timing is synchronized to a crystal running at a multiple of NTSC color subcarrier frequency. Any unit to be used as a transmitter, should be set to GEN. Any unit that will be used only receiver, should be set to LINE. Color receivers should be set to XTAL. | X | X |

Internal Controls

| Control | Location | Function |
|---|---|---|
| Input Level | 1KHz FM Receive BD | Sets the amplitude of the FM signal into the FM demodulator. Set at the factory for normal phone line levels. |
| Symmetry | 1KHz | Sets the DC level at which the Receive BD incoming FM signal is sliced. Set at the factory for normal phone line response. Improper adjustment is indicated by a granular "woodgrain" pattern in the received picture. |
| Black Level | 1KHz FM Receive BD | Sets the DC level of the demodulated input signal at the input to the A/D converter. Set at factory so the BLACK indicator light blinks when full blacks are present in incoming signal. |
| Gain | 1KHz FM Receive BD | Sets the amplitude of the demodulated input signal at the input to the A/D converter. Set a factory so that WHITE indicator light blinks occasionally on peak white signals. |
| Delay | 1KHz FM Receive BD | Sets the window for A/D conversion to correspond with the sample time. Set at factory. |
| Start Burst Frequency | 1KHz FM Receive BD | Sets the capture frequency of the start burst detector. Set at factory 787 Hz. |
| Black Level Frequency | 1KHz FM Transmit BD | Sets the frequency transmitted as black in the FM output |

-continued

| | | |
|---|---|---|
| | | signal. Set at factory for 1800 HZ. |
| Deviation | 1KHz FM Transmit BD | Sets the frequency transmitted white in the FM output signal Set at factory for 2500 Hz. |
| Output | 1KHz FM | Sets the amplitude of the FM output. |
| Level | Transmit BD | Set at factory for 2V p-p into 600 ohms. |
| Line Sync Amplitude | 1KHz FM Transmit BD | Sets the amplitude of the Line Sync pulse. Set at factory for 1:2 ratio of sync to video |
| Lock Adj | Sync & Timing BD | Sets the gen lock to middle of range. |
| Horizontal | Sync & Timing BD | Determines the location of the left side of the raster in the video output display. Normally set to EI RS-170. |
| Output | Memory & Display BD | Controls the amplitude of the video portion of the video output signal. |
| Offset | Memory & Display BD | Controls the black level of the video portion of the video output signal. |

APPENDIX IV—VIDEO FRAME STORE

Purpose of Equipment

The Video Frame Store is a solid-state video memory with high-speed analog/digital (A/D) and digital-/analog (D/A) converters, and is capable of digitizing storing, and displaying a single frame of video information. It can be used to grab and freeze one frame from a camera or video tape recorder and display it on a standard TV monitor for observation. Individual picture elements in the store picture can then be accessed by a computer, processed, and returned to the video frame store memory for redisplay.

Description of Equipment

The Video Frame Store is a digital semiconductor memory made up of random access memory (RAM) integrated circuits capable of storing one complete frame Of video information. Data can be entered into this memory from a camera or other video source by means of high-speed A/D converter in the video frame store or, alternately, entered directly from a computer if a computer I/0 module is installed. The contents of the memory can be continuously viewed on an external TV monitor connected to the video frame store.

The Video Frame Store utilizes standard 2:1 interlace and "dot Interlace" which increases subjective horizontal resolution.

The "frame grab" process can be initiated by means of a front panel pushbutton switch, a remote pushbutton switch, or a TTL store signal. The unit stores the first frame following the conclusion of a store command. The video output is a standard video signal synchronized with the vide input and can be switched or mixed with other video signals or recorded on conventional video tape recorders.

The Video Frame Store can be easily interfaced with most computers or other digital processing equipment. A single 16 bit duplex I/O module in the computer 491 is all that is required for interfacing to most modern computers. All digital signals to or from the unit are buffered and are TTL compatible.

| Specifications | |
|---|---|
| Size: | 3¼" × 19" × 15" (2 memory max.) (5¼" × 19" × 15" 4 memory max.) |
| Weight: | 16 lbs. (20 lbs. for 5¼" chassis) |
| Mounting: | Standard 19" rack |
| Construction: | Solid-state, card file |
| Power: | 117 VAC, 70 Hertz single phase, 100 VA (100 VAC, 230 VAC, and 625-line/50 Hz. optional) |
| Inputs/Video: | Composite video; 1 Vp-p, 75 ohms |
| Inputs/Digital: | Store: Pulse, ground true, 1 microsec. min. (Memory select on multi-memory configurations) |
| Outputs/Video: | Composite, 1 V p-p, 75 ohms |
| Controls: | AC Power: On/Off Store (can be remoted) Video Level Black Level |
| Indicators: | Power |
| Performance: | Resolution: 512 × 512 picture elements, dot interlaced; TV test chart resolution is 400 lines. |
| Frame Time: | Grab: 33 msec. (Computer access: 1 Sec. with optional 793 I/0 Module) |
| Grayscale: | Standard: 8 bits (256 level) Options: 1 to 7 bits |
| Conversion Linearity: | ±0.2%; ± ¼ LSB |
| Video Band width: | 5 MHz |
| Video Source: | The source of the video signal for the Video Frame Store must have the following characteristics: 1. It must be composite (i.e. a mixture of video and synchronizing pulses). Most modern cameras have composite video outputs. 2. It must have 2:1 interlace scanning format. All cameras meeting either U.S. standard EIA RS-170 or EIA RS-330 have 2:1 interlace. Cameras with random interlace will not work (many of the least expensive surveillance cameras have random interlace). |
| Video Monitor | The video monitor connected to the Video Out connector of the video frame store can be any standard monochrome television monitor designed to operate at the line rate of the video input signal. This monitor displays the image stored in the video frame store memory, or, if the STORE pushbutton is held down, can be used to view the video input signal as it is |

-continued

| Specifications |
|---|
| processed through the memory. |

Setting the Video and Black Level Controls

The front panel BLACK LEVEL and VIDEO LEVEL controls are best set by holding the STORE pushbutton down and adjusting the BLACK LEVEL control so there is no loss of detail in the black portions of the picture and adjusting the VIDEO LEVEL control so there is no loss of detail (clipping) in the whitest portions of the picture. These controls can, of course, be set to intentionally alter the store video by clipping either blacks or whites or both.

Controls
Operating Controls (Front Panel)

| Control | Function |
|---|---|
| Power | ON/OFF switch with internal pilot light to indicate when unit is on. |
| Black Level | Controls the DC level of the video signal going to the internal A/D converter. Usually set so that detail in the black portions of the input signal are not lost. |
| Video Level | Controls the amplitude of the video signal going to the internal A/D converter. Usually set so that white details of the input signal are not compressed. |
| Store | Pushbutton switch. The input video is being A/D converted and stored continuously as long as this pushbutton is depressed. Upon release of the button, the 491 stores the next frame. |

Operating Controls (Internal)

| Control | Location | Function |
|---|---|---|
| Lock | Sync, Timing, & A/D Board | Sets the line-sync lock to the middle of its lock-in range. |
| H Width | Sync, Timing, & A/D Board | Determines the location of the left side of the raster in the video output display. |
| Clock | Sync, Timing, & A/D Board | Sets master timing clock control loop to middle of control range. |
| Amplitude | Memory Board | Controls the amplitude of the video portion of the video output signal. |
| Pedestal | Memory Board | Sets the black level setup above blanking. |
| Sync. | Memory Board | Sets Sync level in output video. |

The invention has been described in exemplary and preferred embodiments, but is not limited thereto. Those skilled in the art will recognize that a number of additional modifications and improvements can be made to the invention without departure from the essential spirit and scope. For example, the preferred embodiment of the invention may be used to send other medical related images, such as CT, magnetic resonance and ultrasonic sound images, etc., from the truck to the central headquarters or vice versa. Additionally, the resolution of the images provided are only limited by the resolution of the camera and monitors available to the art. Therefore, the invention is not limited by the above disclosure, but only by the following claims.

I claim:

1. A satellite communication system for sending high resolution, medically related, static images from one or more remote satellite locations to a central location for diagnostics, said satellite communication system comprising:
   each said one or more remote satellite locations comprising:
   means for converting the high resolution images into voltage analog signals;
   means for converting the voltage analog signals into narrow bandwidth and low frequency signals;
   means for transmitting the narrow bandwidth and low frequency signals to a satellite; and
   said central location comprising:
   means for receiving the narrow bandwidth and low frequency signals;
   means for converting the received narrow bandwidth and low frequency signals back into the voltage analog signals;
   means for converting the voltage analog signals into digital signals;
   means for converting the digital signals into high resolution, digitized, medically related images;
   means for transmitting diagnostics of the high resolution, medically related images, in voice or readable form, from the central location to the transmitting remote satellite location.

2. The apparatus of claim 1, further comprising means for buffering the received signals.

3. The apparatus of claim 1, further comprising means for storing the received signals.

4. A method for sending high resolution, medically related, static images from one or more remote satellite locations to a central location for diagnostics, comprising the following steps:
   converting the high resolution images into voltage analog signals at one of said remote locations;
   converting the voltage analog signals into narrow bandwidth and low frequency signals at the remote satellite location;
   transmitting the narrow bandwidth and low frequency signals to a satellite from the remote satellite location;
   receiving narrow bandwidth and low frequency signals at the central location;
   converting the received narrow bandwidth and low frequency signals back into the voltage analog signals at the central location;
   converting the voltage analog signals into digital signals at the central location;
   converting the digital signals into high resolution, digitized, medically related images at the central location:
   transmitting diagnostics of the high resolution, medically related images, in voice or readable form, from the central location to the transmitting remote satellite location.

5. The method of claim 4, further comprising the step of buffering the received signals prior to converting the received signals into high resolution images.

6. The method of claim 4, further comprising the step of storing the received signals.

7. A satellite communication system for sending high resolution, medically related, static images from one or more remote satellite locations to a central location for diagnostics, the satellite communication system comprising:

each of said one or more remote satellite locations comprising:
means for converting the high resolution images into voltage analog signals;
means for converting the voltage analog signals into digital signals;
means for converting the digital signals into narrow bandwidth and low frequency signals;
means for transmitting the narrow bandwidth and low frequency signals to a satellite; and
the central location comprising:
means for receiving narrow bandwidth and low frequency signals;
means for converting the received narrow bandwidth and low frequency signals back into the digital signals;
means for converting the digital signals into high resolution, digitized, medically related images;
means for transmitting diagnostics of the high resolution, medically related images, in voice or readable form from the central location to the remote satellite location.

8. The apparatus for sending high resolution, medical related images from mobile units to the central location of claim 7, further comprising the means for buffering the received signal.

9. The apparatus for sending high resolution, medical related, static images from mobile units to the central location of claim 7, futher comprising the means for storing the received signal.

10. A method for sending high resolution, medically related, static images from one or more remote satellite locations to a central location for diagnostics, the method comprising the steps of:
converting the high resolution images into voltage analog signals at one of the remote satellite locations:
converting the voltage analog signals into digital signals at the remote satellite location;
converting the digital signals into narrow bandwidth and low frequency signals at the remote satellite location;
transmitting the narrow bandwidth and low frequency signals to a satellite at the remote satellite location;
receiving narrow bandwidth and low frequency signals at the central location;
converting the received narrow bandwidth and low frequency signals back into the digital signals at the central location;
converting the digital signals into high resolution, digitized, medically related images at the central location:
transmitting diagnostics of the high resolution, medically related images, in voice or readable form from the central location to the transmitting remote satellite location.

11. The method of claim 10, further comprising the step of buffering the received signals prior to converting the received signals into high resolution images.

12. The method of claim 10, further comprising the step of storing the received signals.

* * * * *